United States Patent [19]

Isogai et al.

[11] Patent Number: 5,463,430
[45] Date of Patent: Oct. 31, 1995

[54] EXAMINATION APPARATUS FOR EXAMINING AN OBJECT HAVING A SPHEROIDAL REFLECTIVE SURFACE

[75] Inventors: Naoki Isogai, Nishio; Yoshiaki Mimura, Gamagori; Masanao Fujieda, Toyohashi, all of Japan

[73] Assignee: Nidek Co., Ltd., Aichi, Japan

[21] Appl. No.: 98,786

[22] Filed: Jul. 29, 1993

[30] Foreign Application Priority Data

Jul. 31, 1992 [JP] Japan .................................. 4-224896
Mar. 31, 1993 [JP] Japan .................................. 5-098942

[51] Int. Cl.$^6$ ........................... A61B 3/10; A61B 3/107; G01B 11/24
[52] U.S. Cl. .................. 351/208; 351/211; 351/212; 351/221; 356/376
[58] Field of Search ..................... 351/208, 211, 351/212, 205, 221; 356/376

[56] References Cited

U.S. PATENT DOCUMENTS

| | | | |
|---|---|---|---|
| 4,660,946 | 4/1987 | Nakamura et al. | 351/212 |
| 4,764,006 | 8/1988 | Hamano et al. | 351/212 |
| 4,917,458 | 4/1990 | Matsumura | 351/212 |
| 5,212,505 | 5/1993 | Penney | 351/208 |
| 5,302,979 | 4/1994 | Maeda et al. | 351/212 |

FOREIGN PATENT DOCUMENTS 61-85920  5/1986  Japan .

*Primary Examiner*—William L. Sikes
*Assistant Examiner*—David R. Parsons
*Attorney, Agent, or Firm*—Finnegan, Henderson, Farabow, Garrett and Dunner

[57] ABSTRACT

An examination apparatus for examining an object having a spheroidal reflecting surface provides a first index projecting optical system for projecting a first measuring index onto the object to be examined at a designated angle, a second index projecting optical system for projecting a second measuring index having a different optical distance from the first index onto the object at the designated angle, so that each reflected images of the first and second measuring index have a designated image height relationship therebetween when the object is placed at a designated working distance, and respective image height of reflected images of the first and second measuring index are detected by a detecting optical system with a photoelectric conversion apparatus, whereby whether the working distance between the object and the apparatus is right or not is judged by processing a signal detected by the photoelectric conversion apparatus.

15 Claims, 7 Drawing Sheets

EXAMINATION APPARATUS FOR EXAMINING AN OBJECT HAVING A SPHEROIDAL REFLECTIVE SURFACE

BACKGROUND OF THE INVENTION

1. Field of the Invention

The present invention relates to an examination apparatus for examining an object having a spheroidal reflecting surface, and more particularly to a detecting mechanism for detecting the alignment condition between the examination apparatus and the object to be examined.

2. Description of Related Art

In an examination apparatus for examining the optical characteristics of an object, there is conventionally an ophthalmic apparatus such as a cornea shape measuring apparatus, an eye refractometer and a keratometer and the like.

Such ophthalmic apparatus comprises usually a known alignment detecting device that utilizes the first Purkinje image to be formed on the examinee's eye by cornea reflection. More specifically, while observing at TV monitor or the like, the examiner moves the measuring part of the ophthalmic apparatus relatively to the examinee's eye so that the first Purkinje image and an alignment reticle of the ophthalmic apparatus are displayed at each position having a determined relation therebetween on the monitor, then the first Purkinje image is also focused on. The above apparatus utilizing the first Purkinje image is provided with measures to prevent alignment error occurring by illuminating the examinee's eye with the collimated luminous flux, for instance.

Incidentally, the alignment in this specification comprises, unless a particular notice, both alignment between the apparatus and the object to be examined in the longitudinal and lateral directions and the same in the optical axis direction.

There is also known another alignment mechanism in which alignment luminous flux is projected onto the examinee's eye from oblique above position, and a light detector may detect the maximum brightness level when the cornea apex and the apparatus are placed respectively at each determined position.

However, in the former apparatus using the first Purkinje image, if the apparatus is moved forward or backward than a position where the first Purkinje image is in focus, the image may become similarly greatly out of focus in either direction. It is consequently difficult to detect the alignment condition, and also to focus on the first Purkinje image to determine a designated working distance. Accordingly, it is substantially impossible to prevent the alignment error occurring.

In the latter alignment mechanism, there is a problem that the scope for detecting the alignment condition is narrowly limited because the light detector has only a small detecting range.

SUMMARY OF THE INVENTION

The present invention has been made in view of the above circumstances and has an object to overcome the above problems and to provide an examination apparatus for examining an object having a spheroidal reflecting surface, which is capable of precisely and simply detecting the alignment condition between the apparatus and the object to be examined.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an examination apparatus for examining an object having a spheroidal reflecting surface of this invention comprises a first index projecting optical system for projecting a first measuring index onto the object to be examined at a designated angle, a second index projecting optical system for projecting a second measuring index having a different optical distance from the first index onto the object at the designated angle, so that reflected images of the first and the second measuring index have a designated image height relationship therebetween when the object is placed at a designated working distance, a detecting optical system for detecting the reflected images of the first and second indexes with a photoelectric conversion apparatus, and a judging means for judging whether the working distance between the object and the apparatus is right, by processing a signal detected by the photoelectric conversion apparatus.

In the second aspect of the present invention, an ophthalmic apparatus for examining an examinee's eye comprises a first index projecting optical system for projecting a first point light source at infinity onto the examinee's eye at a designated angle, a second index projecting optical system for projecting a second point light source at finity onto the same meridional plane of the examinee's eye at the designated angle, and a detecting optical system for detecting through a photoelectric conversion apparatus respective image height of reflected images formed by the first and the second point light sources, and a judging means for judging whether the working distance between the object and the apparatus is right, by processing a signal detected by the photoelectric conversion apparatus.

In the third aspect of the present invention, an ophthalmic apparatus comprises an observing optical system for observing an anterior part of an examinee's eye, an aiming mark observing optical system for introducing an aiming mark having a size comparable with the cornea size of the examinee's eye through optical deflecting means arranged in the observing optical system into the observing optical system, index projecting optical system for projecting a first index and a second index onto the examinee's eye, each index having a different optical distance, a detecting optical system for detecting respective cornea reflected images of the first and second indexes projected through the index projecting optical system to the examinee's eye, and a judging means for judging whether a distance between the examinee's eye and a focusing lens is right by processing a signal detected by the detecting optical system.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention.

In the drawings.

DETAILED DESCRIPTION OF THE PREFERRED EMBODIMENTS

A detailed description of preferred embodiments of an examination apparatus for examining an object having a spheroidal surface embodying the present invention will now be given referring to the accompanying drawings.

Figure 1:
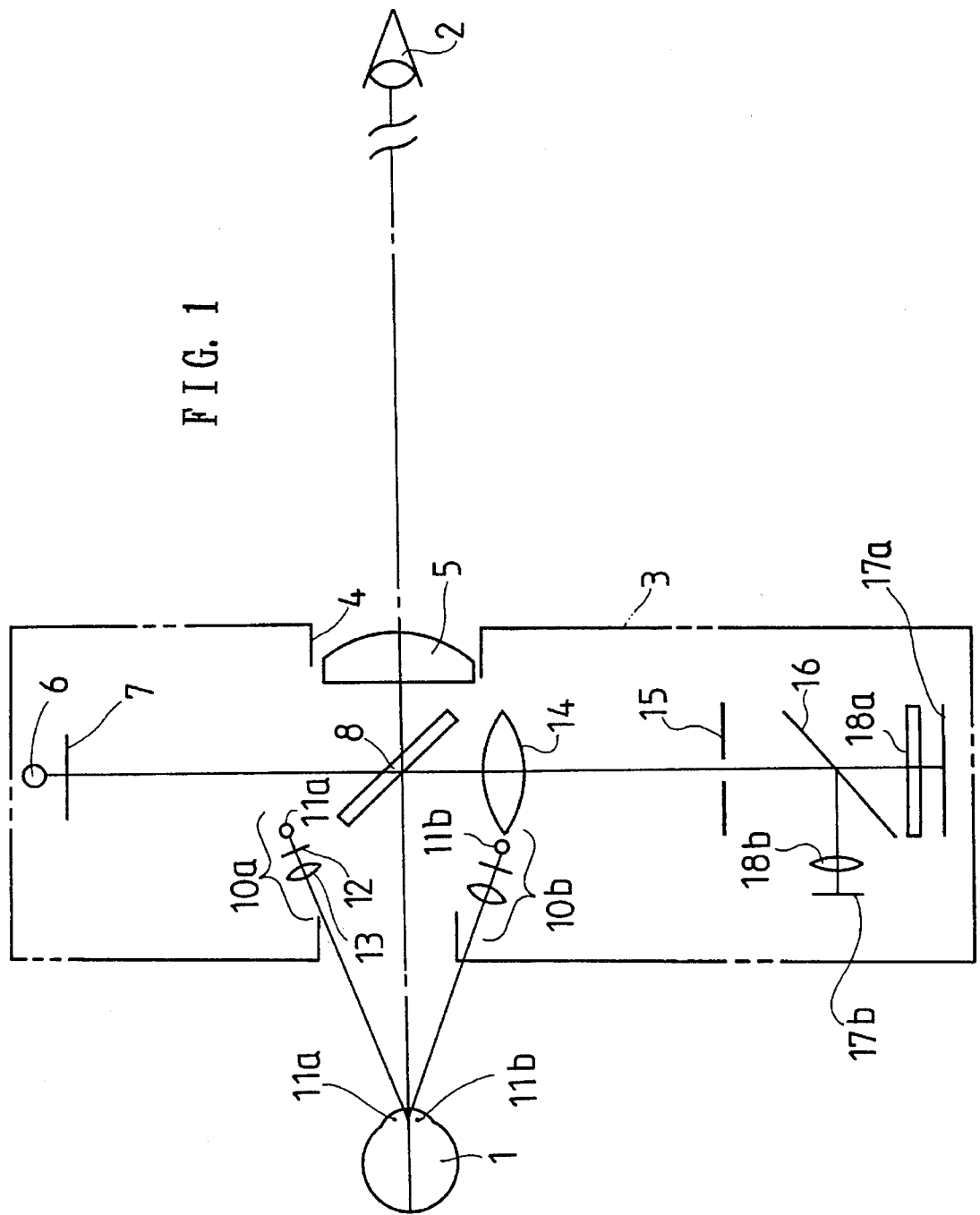
FIG. 1 is an optical arrangement diagram of the ophthalmic apparatus in one embodiment of the present invention.

In FIG. 1 showing an optical arrangement taken a side view of an optical system, the apparatus body of box type 3 is provided with a through hole 4 in which an observing lens 5 is fitted, and the examiner's eye 2 observes in binocular vision the examinee's eye 1 through the observing lens 5. The observing lens 5 is for magnifying the examinee's eye 1, for example, if the examinee's eye 1 is 75 mm away from the observing lens 5, the examiner's eye 2 is 200 mm away from the same and the observing lens 5 has 250 mm focusing distance, the magnified image is then 1.28 times as large as the actual image.

Figure 2:
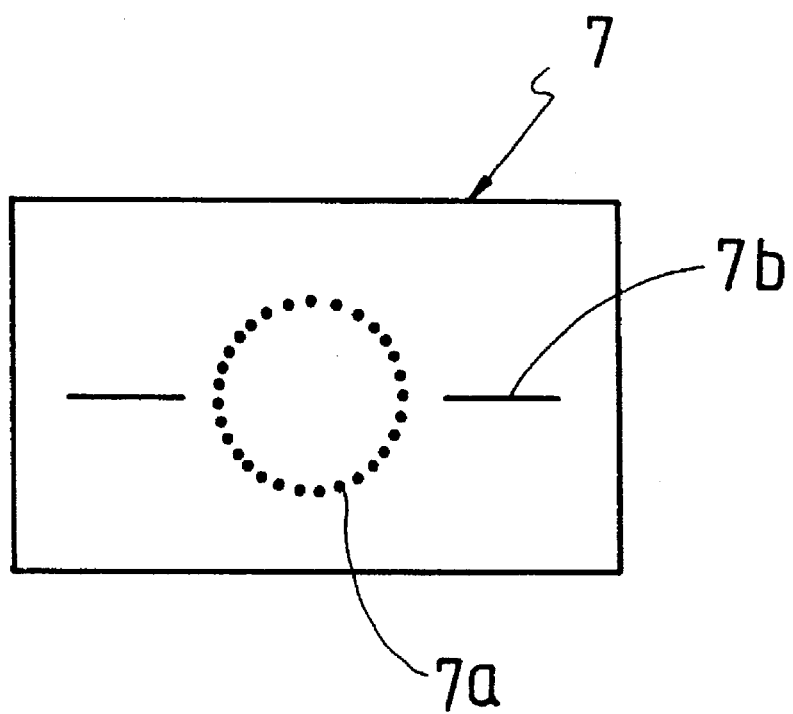
FIG. 2 is a constructive diagram of showing an aiming mark plate in the optical system shown in FIG. 1.

In the apparatus body 3, an illumination light source 6 comprising two colors LED; yellow and red, an aiming mark plate 7, a beam splitter 8 arranged on the optical path of the observing system, and index projecting optical systems 10a–10d for measuring cornea shape of the examinee's eye. The aiming mark plate 7 provides, referring to FIG. 2, a circular dot mark 7a having the almost same diameter as cornea outline; for instance 11 mm diameter in this embodiment, being a little smaller than the mean horizontal diameter of cornea of the Japanese (there is little differences among individuals of the cornea diameter), and lines 7b indicating that an astigmatic axis of a measuring system is 0 degree direction. It is also possible to add another lines indicating that an astigmatic axis is 90 degree direction.

The light emitted from the illumination light source 6 passes through the aiming mark plate 7, and is reflected by the beam splitter 8 toward the examiner's eye 2.

In the optical characteristic of light beam splitting member such as the beam splitter 8, various transmitting/reflecting characteristics can be selected in consideration of a wavelength of the aiming mark, the same of measurement light and the arranging position of the light beam splitting member.

The index projecting optical systems 10a–10d (10c and 10d are not shown) are arranged at 90-degree angle apart from each other in a same circle centering the optical axis, each of which is constituted of a LED 11 for emitting light of near infrared area, a spot diaphragm 12 and a collimator lens 13. When detecting a working distance (alignment condition), the collimator lens 13 of the index projecting optical system 10a is disposed out of the optical path so that the light source (LED 11) may be put to finity.

The apparatus body 3 is further internally equipped with a measurement optical system consisted of a focusing lens 14, a telecentric diaphragm 15 arranged at a focus point of the focusing lens 14, a beam splitter 16 for dividing light into two light beams, one-dimensional image sensors 17a and 17b respectively arranged on each optical path of two light beams so as to cross both detecting directions of the image sensors 17a and 17b, and cylindrical lenses 18a and 18b. The cylindrical lenses 18a and 18b are respectively arranged between the telecentric diaphragm 15 and each of the one-dimensional image sensors 17a and 17b so as to correspond respective axes of the cylindrical lenses 18a and 18b with respective detecting directions of the image sensors 17a and 17b.

The above optical system is designed so that an optical path between the beam splitter 8 and the aiming mark plate 7 and an optical path between the beam splitter 8 and the cornea outline section of examinee's eye 1 may have the same length respectively when the examinee's eye 1 is apart from the focusing lens 14 by a designated distance, and the alignment between the measuring optical system and the examinee's eye 1 may be right when the aiming dot mark 7a substantially corresponds with the cornea outline of the examinee's eye 1. Accordingly, if the apparatus is adjusted so as to coincide the size of the aiming dot mark 7a with the size of the cornea outline section which is a border between cornea and sclera, the examiner can observe clearly the examinee's eye in correct alignment even through an apparatus for observing directly the examinee's eye.

Figure 3:
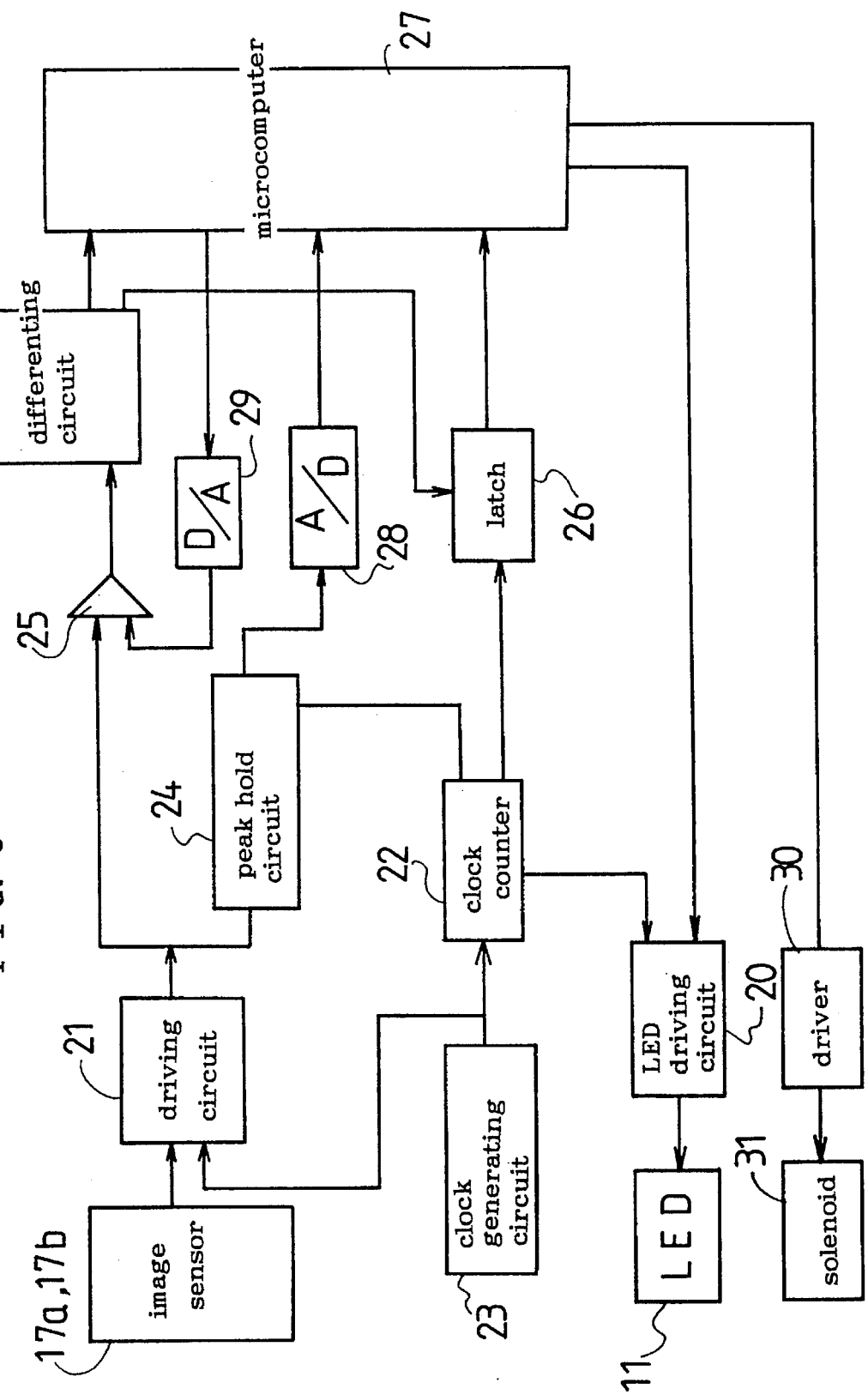
FIG. 3 is a block diagram of explaining the electric control operation of the optical system of the present invention.

FIG. 3 shows a block diagram of electric control system in the above examination apparatus. In the electric control system, a LED driving circuit 20 for driving four LED 11 (point sources), a driving circuit 21 for detecting signals on the one-dimensional image sensors (CCD) 17a and 17b, a clock counter 22, a clock generating circuit 23, a peak hold circuit 24 for holding a peak voltage transferred from the driving circuit 21, a comparator 25 for providing a strobe signal by comparing the signal transferred directly from the driving circuit 21 and a half voltage signal converted through a microcomputer 27 from the peak hold circuit 24, a latch 26 to keep counter value from the clock counter 22 when the strobe signal is given to the microcomputer 27, an A/D converter 28 and a D/A converter 29. A driver 30 drives a solenoid 31 to remove the collimator lens 13 of the index projecting optical system 10a out of the optical path, or to insert the collimator lens 13 into the optical path.

The operation of the above electric control system is as follows.

Signals provided by the two image sensors 17a and 17b are transferred through a CCD driving circuit 21 to a comparator 25 and a peak hold circuit 24. A peak voltage detected by the peak hold circuit 24 is converted into a corresponding digital peak signal by the A/D converter 28, and the digital peak signal is given to the microcomputer 27. The digital peak signal corresponding to the peak voltage detected by the peak hold circuit 24 is transferred through the microcomputer 27 to a D/A converter 29, the D/A converter 29 converts the digital peak signal into a half voltage signal corresponding to half the peak voltage, and then the half voltage signal is given to the comparator 25. The comparator 25 compares the half voltage signal with a signal given directly thereto by the CCD driving circuit 21 and provides a strobe signal. When the strobe signal is provided by the comparator 25, a signal provided by a counter 22 is given to a latch 26. The position of a shading edge is determined from the waveform.

Alignment operation with the above mentioned examination apparatus will be explained hereinafter.

Figure 4:
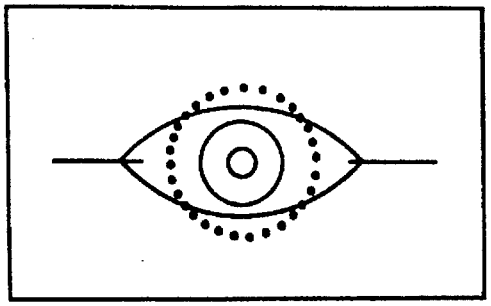
FIGS. 4(a) and 4(b) are respectively diagrams of explaining focus adjustment means to judge whether a working distance is right by comparing both sizes of a cornea image observed through the observing system and the aiming mark.
Figure 4:
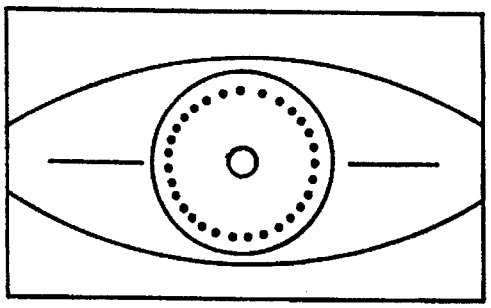

The examiner observes the anterior part of the examinee's eye 1 in the binocular vision through the observing lens 5 and the beam splitter 8, then the examiner can observe also the circular dot mark 7a superimposed on the eye 1. First, for the alignment in the lateral and longitudinal directions between the apparatus and the examinee's eye 1, the examiner moves the examination apparatus so as to superimpose the circular dot mark 7a concentrically on the cornea outline of the examinee's eye 1 while observing the eye 1 through the observing lens 5. And then, by comparing the cornea of the examinee's eye 1 to the circular dot mark 7a, the examiner further roughly judges the working distance is right or not. When the circular dot mark 7a is concentrically superimposed on the anterior part of the examinee's eye 1, the cornea outline is smaller than the circular dot mark 7a if the apparatus is too apart from the examinee's eye 1, as shown in FIG. 4(a), the cornea outline is larger than the circular dot mark 7a if the apparatus is too near the examinee's eye 1 as shown in FIG. 4(b). Accordingly, the apparatus is moved forward or backward so that the examiner may observe the cornea horizontal diameter in about the same size as the circular dot mark diameter, thereby the working distance is roughly adjusted.

Keeping abreast with the above rough adjustment of the working distance, the measurement system of the apparatus detects whether the working distance is right. While the working distance is detected, the collimator lens 13 of the index projecting optical system 10a is out of the optical path thereof to consist a finite light source, so that the respective image height are compared between the cornea reflected images formed by the optical systems 10a (finite light source) and 10b (infinite light source). That utilizes a characteristic that, in a case that the cornea reflected images are respectively formed by an infinite light source and a finite light source, the height of the image formed by the infinite light source is not changed even if the working distance changes, but then the height of the image formed by the finite light source is changed. Additionally, it is possible to utilize finite light sources at different distances from the examinee's eye instead of utilizing the finite source and the infinite light source because the height of the reflected image is also changed according to the distance of the light source.

More specifically, the detecting operation of the working distance is explained as follows.

Point light sources 11c and 11d (not shown) are first turned on. And point images 11c' and 11d' formed by the point light sources 11c and 11d are detected by the image sensors 17a and 17b to find out a coordinate of the center point "O" which is an intermediate position between the two detected points of the images 11c' and 11d'.

Based on the detected coordinate of the center point "O", a length (Oa') from the center point to a point image 11a' and a length (Ob') from the center point to a point image 11b' are respectively found out. The point image 11b' is formed by the point light source 11b having an optical infinite distance, thereby the length "Ob'" is little changed even if the apparatus is moved in the focus direction, referring to FIG. 5(a). On the other hand, the point image 11a' is formed by the point light source 11a having an optical finite distance, thereby the length "Oa'" is changed if the apparatus is moved in the focus direction, referring to FIG. 5(b).

Figure 5:
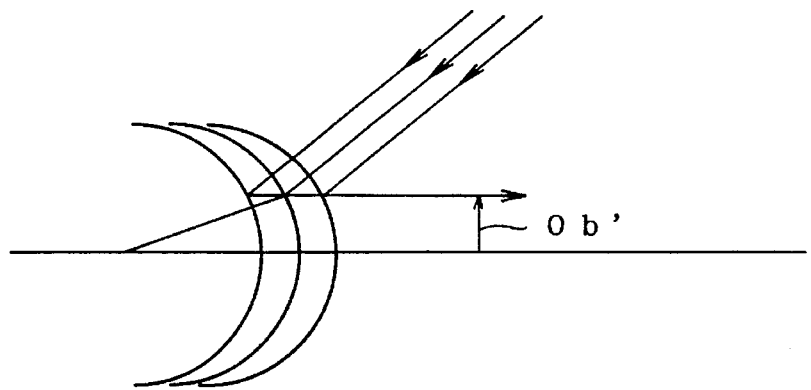
FIGS. 5(a) through 5(c) are respectively diagrams of explaining focus adjustment means to judge whether a working distance is right by comparing each image height of cornea reflected images formed through an index projecting optical system.
Figure 5:
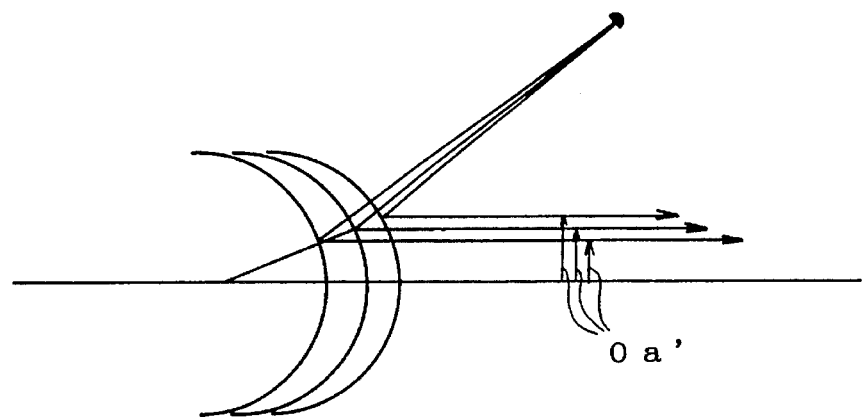
Figure 5:
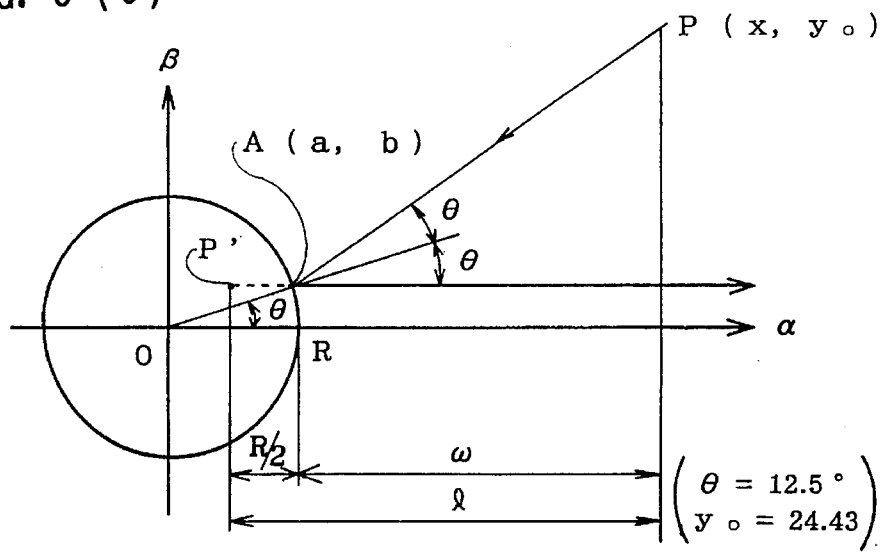

FIG. 5(c) shows a diagram explaining a relation between a position of a finite light source P, the cornea of an examinee's eye and a reflected light beam.

The light beam emitted from the finite light source $P(x, y_o)$ is reflected by the cornea surface at the point A(a, b) thereon, travels in parallel with α-axis. If "x" is changed, namely the finite light source P is moved in the focus direction, the height "b" of the reflected image is given by the following formulas.

$$Ab^4 + Bb^3 + Cb^2 + Db + E = 0$$

where
$A = 4(x^2 + y_o^2)$
$B = 4y_o R^2$
$C = R^2(R^2 - 4x^2 - 4y_o^2)$
$D = 2y_o R^4$
$E = y_o^2 R^4$ A length "l" between P and P' when the height (Oa') of the image formed by the finite light source agrees with the height (Ob') of the image formed by the infinite light source is given by the following formula.

$$l = \frac{R}{2}\left(\frac{1}{\cos\theta} - 1\right) + \frac{yo}{\tan 2\theta}$$

(where l is l=ω+R/2=x−R/2) corresponding with a position where a reflected image is formed by the infinite light source, within from the apical point of the cornea to a half of radius of curvature.

When examined a change of l according to various radius of curvature of the cornea "R" in the above measuring conditions, the result is obtained that Δl had only ±0.03 mm changes in range of R being 5–10 mm.

A working distance between the focusing lens 14 and the examinee's eye 1 is predetermined so as to become Oa'/Ob'=α, where α is a constant and a value of Oa'/Ob' is not influenced by the cornea R. It is further possible to determine the α value so as to be changeable according to a relationship with alignment precision required to the apparatus.

By utilizing the above relation, the alignment between the apparatus and the examinee's eye in the focus direction is judged as follows.

(1) Oa'/Ob'>α: the cornea is dislocated forward than a right focus point
(2) Oa'/Ob'<α: the cornea is dislocated backward than a right focus point
(3) Oa'/Ob'=α: the alignment is completed.

Based on the detected result through the one-dimensional image sensors 17a and 17b, microcomputer judges whether the working distance is right or not by comparing the image height (Oa') of the cornea reflected image of the finite light source with the image height (Ob') of the cornea reflected image of the infinite light source. Then a position where the height Oa' is in agreement with the height Ob' is a right alignment position.

When judged both height of the reflected images to be same in comparison with a designated reference, the microcomputer operates the illumination light source 6 to change the color from red to yellow in order to indicate that the working distance is right. Such information may be also displayed on a monitor or the like through a display circuit.

And the microcomputer transmits a trigger signal to start the measurement of the cornea shape. This measurement and calculation method has been in detail proposed in Japanese Laid-Open Patent Application No. SHO 61(1986)-85920, accordingly the explanation thereof is omitted in this specification.

Figure 7:
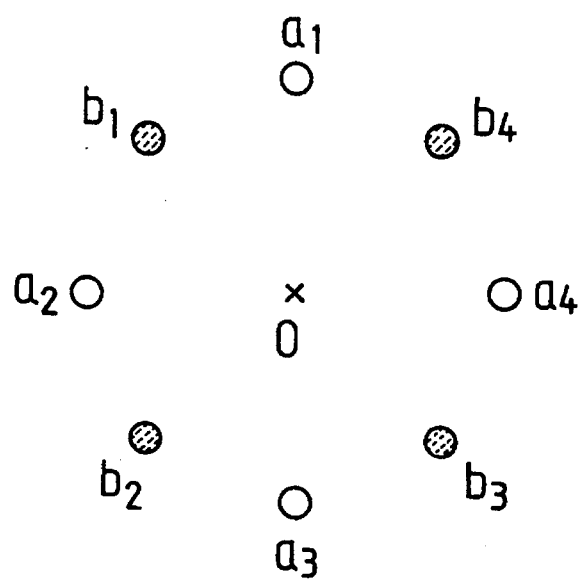
FIG. 7 is an arrangement diagram of measuring indices in the second embodiment according to the present invention.
Figure 8:
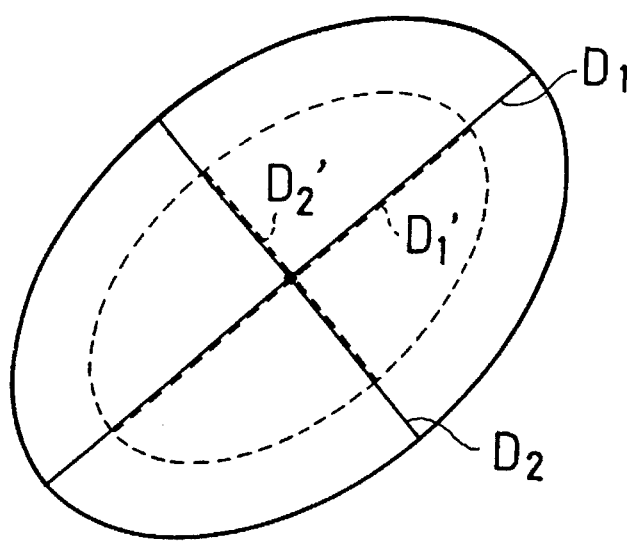
FIG. 8 is a diagram to explain a method to measure radius of curvature and to detect focus adjustment at the same time on the basis of length of minor principal meridian or major principal meridian of measuring indices shown in FIG. 7.

In the second embodiment according to the present invention, measuring indices $a_1$–$a_4$ and $b_1$–$b_4$ are arranged so as to be respectively apart from the optical axis "O" by same distance as shown in FIG. 7, then, a group of infinite indices $a_1$–$a_4$ and a group of finite indices $b_1$–$b_4$ each have a different optical distance. Projecting the infinite indices $a_1$–$a_4$ enable measurement of the radius of curvature of a cornea, whereby, the apparatus in the second embodiment can serve both as the measurement of the radius of curvature of a cornea and alignment detection. Namely, each length or each radius of curvature of major principal meridian and minor principal meridian is found by images of the infinite indices $a_1$–$a_4$ and similarly with the finite indices $b_1$–$b_4$, and then both values are compared with each other to adjust a working distance.

Assuming that the length or radius of curvature of minor principal meridian to be found by images of (infinite) indices $a_1$–$a_4$ is "$D_1$", that of major principal meridian is "$D_2$", and that of minor principal meridian to be found by images of (finite) indices $b_1$–$b_4$ is "$D_1$'", that of major principal meridian is "$D_2$'", values of "$D_1$" and "$D_1$'" or values of "$D_2$" and "$D_2$'" or values of $(D_1+D_2)/2$ and $(D_1'+D_2')/2$ are compared with each other. If the $a_1$–$a_4$ are infinite indices and $b_1$–$b_4$ are finite indices, the above "$D_1$" and "$D_1$'" will indicate following conditions:

(1) D1'>D1: working distance is shorter.
(2) D1'=D1: working distance is correct.
(3) D1'<D1: working distance is longer.

By utilizing the above calculation, the radius of curvature of a cornea shape is measured and, at the same time, focus alignment is also detected.

Figure 9:
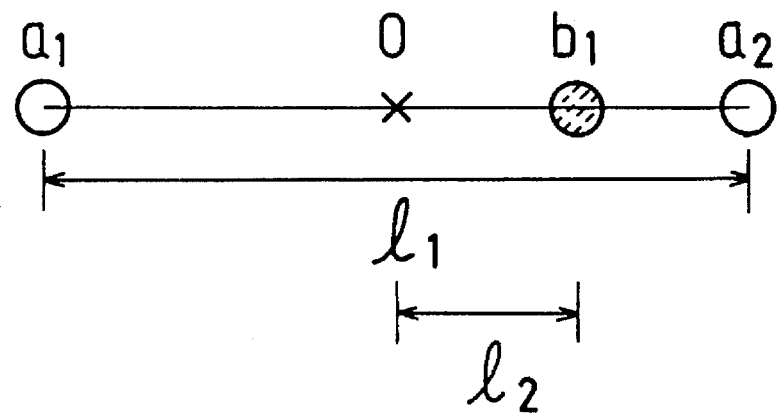
FIGS. 9(a) and 9(b) are arrangement diagrams of measuring indices in the third embodiment according to the present invention.
Figure 9:
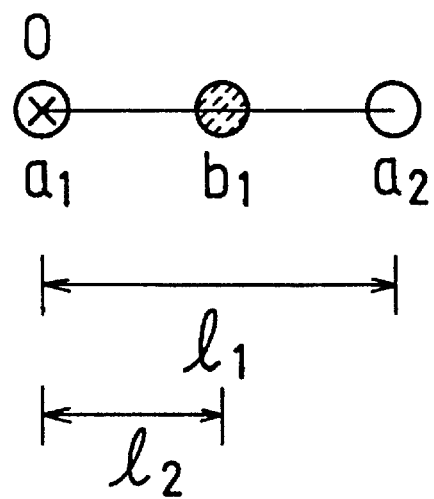

Measuring indices in the third embodiment according to the present invention are arranged as shown in FIGS. 9(a) and 9(b), whereby alignment condition can be detected with at least those indices without being affected by astigmatism.

In FIG. 9(a), indices $a_1$ and $a_2$ are symmetrically disposed apart from the optical axis "O" by same distance each other, and thereby each having a same optical distance, and an index $b_1$ is disposed between the infinite index $a_2$ and the optical axis "O", which has a different optical distance from the optical distances of infinite indices $a_1$ and $a_2$. The index $b_1$ can be also disposed on elongated line of a straight line linking indices $a_1$ and $a_2$, but alignment condition may be detected more simply when the index $b_1$ is disposed between the indices $a_1$ and $a_2$ as shown in FIG. 9(a). The indices $a_1$ and $a_2$ are infinite and the index $b_1$ is finite. Therefore respective height of images of the indices $a_1$ and $a_2$ formed on an object and height of an image of the index $b_1$ are compared with each other, and the working distance is accordingly adjusted. Assuming $l_2/l_1=\alpha$, where $l_1$ is a distance between indices $a_1$ and $a_2$, $l_2$ is a distance between a center of images of indices $a_1$, $a_2$ and an image of index $b_1$, a value of $\alpha$ in a correct working distance is determined on the basis of a designed value $\alpha_o$. By utilizing the above relation, the alignment between the apparatus and the examinee's eye is judged as follows.

(1) $\alpha>\alpha_o$: working distance is shorter
(2) $\alpha=\alpha_o$: working distance is correct
(3) $\alpha<\alpha_o$: working distance is longer In FIG. 9(b), measuring index $a_1$ is disposed on the optical axis "O" by half mirror or the like, the arrangement corresponding to a method using fixation lamp, the index $a_1$ can be also used as fixation index. In this case, the alignment is similarly detected by comparing a relation between value of $l_2/l_1=\alpha$ and the designed value $\alpha_o$, where $l_1$ is same as above, and $l_2$ is a distance between indices $a_1$ and $b_1$.

The present invention may be embodied in other specific forms without departing from the spirit or essential characteristics thereof. For instance, the alignment is detected based on each height of point light images 11a' and 11b' in this embodiment, but then, if detected based on data before and after the change of the optical distance when the point light source 11a has a changeable optical distance as described above, it is possible to prevent the influence by the irregular astigmatism.

If a cornea reflecting luminescent spot is formed on a visual axis of the examinee's eye by an infinite light projected from a front side of the examinee's eye, it is easy to find out the center point "O" and also possible to utilize any other light source than point light source.

In the above embodiment, apparatus moving device to the examinee's eye is not specifically described, because the above embodiment supposes that the present invention is applied to a hand-held type apparatus, but the present invention can be also applied to a known fixed joystick type apparatus.

Figure 6:
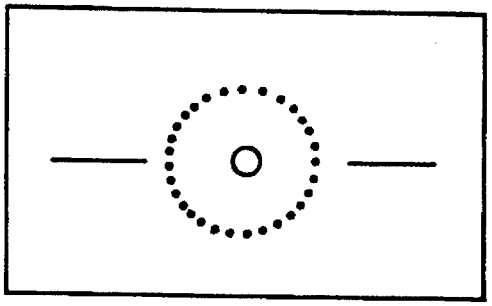
FIG. 6 is a constructive diagram of showing another aiming mark plate in the optical system shown in FIG. 1.

If the present invention is applied to an apparatus limited in the minimum pupil diameter necessary to measure, such as an eye refractometer, the apparatus may be provided with, for the aiming mark, a ring or circular dot points corresponding to the minimum pupil diameter as shown in FIG. 6.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An examination apparatus for examining an object having a spheroidal reflecting surface, the apparatus comprising:

a first index projecting optical system, having an optical distance, for projecting a first measuring index onto the object to be examined at a designated angle;

a second index projecting optical system for projecting a second measuring index, having an optical distance different from the optical distance of the first index, onto the object at said designated angle, so that reflected images of the first and second measuring index have a designated image height relationship therebetween when the object is placed at a designated working distance;

a detecting optical system for detecting the reflected images of the first and second indices with a photoelectric conversion apparatus; and judging means for judging whether the working distance between the object and the apparatus is correct, in accordance with a signal detected by the photoelectric conversion apparatus.

2. An examination apparatus according to claim 1, wherein the examination apparatus comprises an ophthalmic apparatus for examining an examinee's eye, wherein the first measuring index is projected at an infinite optical distance and the second index is projected at a finite optical distance.

3. An examination apparatus according to claim 1, wherein said detecting optical system comprises a telecentric optical system including a focusing lens having a focal distance such that an index image formed on the cornea and the photoelectric conversion apparatus are arranged with a conjugate relation therebetween, and a diaphragm positioned at a focal point of the focusing lens.

4. An examination apparatus according to claim 1, further comprising information means responsive to the judging means for informing an examiner of the correctness of the working distance between the object and the apparatus.

5. An ophthalmic apparatus for examining an examinee's eye, the apparatus comprising:

a first index projecting optical system for projecting a first point light source at infinity onto a meridional plane of the examinee's eye at a designated angle;

a second index projecting optical system for projecting a second point light source at a finite distance onto the same meridional plane of the examinee's eye at said designated angle;

a detecting optical system for detecting through a photoelectric conversion apparatus respective image height of reflected images formed by the first and second point light sources; and judging means for judging whether the working distance between the object and the apparatus is correct, in accordance with a signal detected by the photoelectric conversion apparatus.

6. An ophthalmic apparatus according to claim 5, further comprising:

an observing system, having an optical axis, to observe the examinee's eye;

a mark forming means for forming an aiming mark of luminous flux having a size comparable to the cornea size of the examinee's eye, which is disposed at a substantially conjugate position with an anterior part of the examinee's eye when the working distance is correct; and a light beam splitting member for transmitting the luminous flux of said mark forming means to the examinee's eye, said light beam splitting member being positioned on the optical axis of said observing system;

wherein the alignment is judged to be correct or incorrect through a comparison between the cornea size of the examinee's eye and the size of the aiming mark.

7. An ophthalmic apparatus according to claim 5, further comprising:

a trigger signal generating means for transmitting a trigger signal to drive a detecting section when the judging means judges the working distance between the examinee's eye and the apparatus to be correct.

8. An examination apparatus according to claim 5, further comprising information means responsive to the judging means for informing an examiner of the correctness of the working distance between the object and the apparatus.

9. An ophthalmic apparatus, comprising:

an observing optical system for observing an anterior part of an examinee's eye;

an observing optical system, having an optical deflecting means for introducing into said observing optical system, an aiming mark having a size comparable to the cornea size of the examinee's eye;

index projecting optical system for projecting a first index and a second index onto the examinee's eye, each said first and second index having a different optical distance;

a detecting optical system for detecting respective cornea reflected images of said first and second indices projected through said index projecting optical system to the examinee's eye; and judging means for judging whether a distance between the examinee's eye and a focusing lens is correct in accordance with a signal detected by said detecting optical system.

10. An ophthalmic apparatus according to claim 9, wherein said index projecting optical system is provided with a collimator lens movable in and out of said optical system to project one of the first and second indices at an infinite distance and another at a finite distance.

11. An ophthalmic apparatus according to claim 10, wherein said detecting optical system detects image height of a reflected image projected by the light having the infinite optical distance with said collimator lens inserted in the optical path, and image height of a reflected image projected by the light having the finite optical distance with said collimator lens removed from the optical path, said judging means judges whether a working distance is correct by comparing both image height of the reflected image by the light having the finite optical distance and by the light having the infinite optical distance, each image being detected through said detecting optical system.

12. An ophthalmic apparatus according to claim 9, wherein the index projecting optical system includes a first index projecting optical system for projecting the first index and a second index projecting optical system for projecting the second index.

13. An ophthalmic apparatus according to claim 9, wherein said optical deflecting means comprises a beam splitter for transmitting a reflected image of the examinee's eye and reflecting said aiming mark image, said beam splitter being movable toward the examinee's eye.

14. An ophthalmic apparatus according to claim 9, further comprising information means responsive to the judging means for informing an examiner of the correctness of the distance between the examinee's eye and a focusing lens.

15. An ophthalmic apparatus according to claim 9, further comprising a trigger signal generating means for transmitting a trigger signal to drive a detecting section at times when said judging means judges a correct distance between the examinee's eye and the focusing lens.

* * * * *